United States Patent

Cossement et al.

Patent Number: 5,478,941
Date of Patent: Dec. 26, 1995

[54] ENANTIOMERS OF 1-[(4-CHLOROPHENYL)PHENYLMETHYL]-4-[(4-METHYLPHENYL)SULFONYL]PIPERAZINE

[75] Inventors: Eric Cossement, Brussels; Guy Bodson, Bellefontaine; Jean Gobert, Brussels, all of Belgium

[73] Assignee: U C B, S.A., Brussels, Belgium

[21] Appl. No.: 207,096

[22] Filed: Mar. 8, 1994

[30] Foreign Application Priority Data

Mar. 15, 1993 [GB]  United Kingdom .......... 9305282

[51] Int. Cl.⁶ .......... C07D 295/26; C07D 295/088; C07D 295/073; C07D 295/104
[52] U.S. Cl. .......... 544/383; 544/396; 564/90; 564/321
[58] Field of Search .......... 544/383, 396

[56] References Cited

U.S. PATENT DOCUMENTS

| | | | |
|---|---|---|---|
| 3,406,174 | 10/1968 | Houlihan | 260/268 |
| 4,525,358 | 6/1985 | Baltes et al. | 514/255 |
| 4,968,676 | 11/1990 | Zipperer et al. | 514/183 |
| 5,087,627 | 2/1992 | Morita et al. | 544/396 |

FOREIGN PATENT DOCUMENTS

| | | |
|---|---|---|
| 523901 | 4/1954 | Belgium . |
| 568380 | of 1959 | Canada . |
| 0058146 | 8/1982 | European Pat. Off. . |
| 752331 | 7/1956 | United Kingdom . |
| 2225321 | 5/1990 | United Kingdom . |

OTHER PUBLICATIONS

Kato et al, *Chemical Abstracts*, vol. 78, No. 148000 (1973).

*Primary Examiner*—Emily Bernhardt
*Attorney, Agent, or Firm*—Wenderoth, Lind & Ponack

[57] ABSTRACT

Levorotatory and dextrorotatory enantiomers of 1-[(4-chlorophenyl)phenylmethyl]-4-[(4-methylphenyl)sulfonyl]piperazine of the formula

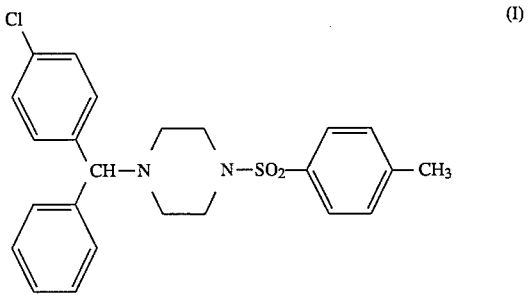

(I)

their preparation and use for the preparation of substantially optically pure enantiomers of 1-[(4-chlorophenyl)phenylmethyl]piperazine, which are themselves valuable intermediate products for the preparation of optically active therapeutic compounds having a very high degree of optical purity.

3 Claims, No Drawings

ENANTIOMERS OF 1-[(4-CHLOROPHENYL)PHENYLMETHYL]-4-[(4-METHYLPHENYL) SULFONYL] PIPERAZINE

The present invention relates to new compounds, the substantially optically pure levorotatory and dextrorotatory enantiomers of 1-[(4-chlorophenyl)phenylmethyl] -4]-[(4-methylphenyl)sulfonyl]piperazine of the formula

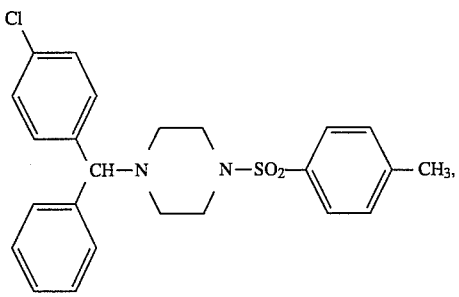

(I)

to a process for the preparation of these compounds and to their use for the preparation of substantially optically pure levorotatory and dextrorotatory enantiomers of 1-[(4-chlorophenyl)phenylmethyl]piperazine. The latter compounds, are valuable intermediates for the preparation of substantially optically pure therapeutically active compounds, in the levorotatory and dextrorotatory forms.

These therapeutically active compounds may be used in the treatment of asthma, allergies, inflammation and anxiety, and as sedative or tranquilizing agents. A property frequently, observed with these compounds is their high degree of peripheral and/or central antihistaminic activity, as the basis for their use as a drug.

It is well known that the biological properties of many compounds, such as for example drugs, hormones, herbicides, insecticides or sweetening agents, are influenced by stereochemical factors. The importance of the relationships between the optical activity and the biological properties, has been stressed since 1926 (A. R. CUSHNY, Biological Relations of Optically Isomeric Substances, Williams and Williams Co., Baltimore, 1926). Since that time, many examples abound which have confirmed the now generally accepted principle that a racemic compound and its levorotatory and dextrorotatory enantiomers should be considered as entirely distinct pharmacological entities. The optical activity, which is an image of the asymmetrical structure of an organic compound is one of the important factors which govern the pharmacological activity of this compound and its biological response. Indeed, according to whether the levorotatory or dextrorotatory form of a drug is used, considerable differences in the properties, such as its transport, its distribution in the organism or its elimination can appear. These properties are decisive for the concentration of the drug in the organism or its exposure time at the site of activity. Furthermore, the pharmacological activity of the two isomers can differ considerably. For example, one enantiomer may be much more active than the other or, in a border-line case, this enantiomer could possess alone all the pharmacological activity, the other being totally inactive and serving only as a simple diluent. It can also occur that the pharmacological activities of the two isomers are different, which produces consequently two compounds having distinct therapeutic properties. Moreover, the metabolism and the toxicity can be very different from one isomer to another, so much so that one of the optically active isomers can be more toxic than the other. One of the most striking examples in this field is that of thalidomide, where the two enantiomers possess similar hypnotic effects but only the S enantiomer has teratogenic effects.

Finally, it has also to be added that the optical isomers are useful as probes which are of uttermost importance in the study of chemical interactions with physiological mechanisms (for example, the selectivity of binding to a receptor).

That is the reason why many pharmaceutical laboratories devote much time and efforts to isolate or synthesize the enantiomers of pharmacologically active compounds and to study the therapeutic properties thereof.

A process for the preparation of the enantiomers of 2-[2-[4-[(4-chlorophenyl)phenylmethyl] -1-piperazinyl] ethoxy]acetic acid dihydrochloride, known as a non-sedative antihistamine drug under the generic name of cetirizine, is described in British Patent No. 2,225,321. This process is based on the use of levorotatory or dextrorotatory 1-[(4-chlorophenyl)phenylmethyl]piperazine as starting material. In that patent, the enantiomers of 1-[(4-chlorophenyl)phenylmethyl]piperazine are obtained by chemical resolution of the racemic form, using conventional methods, in particular, by salt formation with a suitably selected optical isomer of tartaric acid.

The major disadvantages of this process are, on the one hand, that the yield of the resolution step of the racemic 1-[(4-chlorophenyl)phenylmethyl]piperazine is extremely low (only 12.7%) and, on the other hand, that the optical purity of the dextrorotatory and levorotatory enantiomers so obtained is insufficient and does not allow the final product to be prepared with an optical purity greater than 95%.

Consequently, it appears to be very desirable to provide new routes for preparing the enantiomers of 1-[(4-chlorophenyl)phenylmethyl]piperazine with improved optical purity and in better yields and, thereby, to provide excellent starting materials to produce optically active isomers of useful drugs with a very high degree of optical purity.

But, to achieve this object, it is necessary to find precursors having already the correct stereochemical configuration and which, on the one hand, can be themselves prepared relatively simply and economically with satisfactory optical purity, and, on the other hand, which can be converted easily and with high yields into the substantially optically pure enantiomers of 1-[(4-chlorophenyl)phenylmethyl]piperazine.

We have now discovered a new compound, 1-[(4-chlorophenyl)phenylmethyl] -4-[(4-methylphenyl)sulfonyl]piperazine, the levorotatory and dextrorotatory forms of which comply perfectly with this object.

Accordingly, the present invention provides as new compounds, the levorotatory and dextrorotatory enantiomers of 1-[(4chlorophenyl)phenylmethyl] -4-[(4i-methylphenyl)sulfonyl]piperazine of the formula

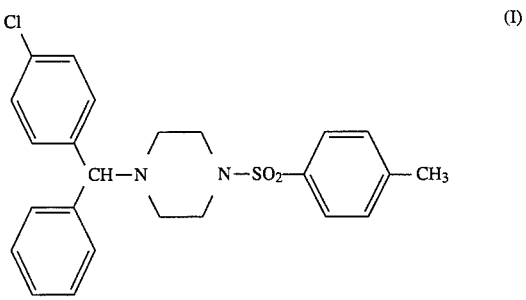

(I)

According to the present invention, the enantiomers of the compound of formula I are advantageously in a substantially optically pure form.

In the present specification, by "substantially optically pure", is meant an optical purity greater than 98% and this optical purity corresponds to the percent excess of the optically active isomer present in major amount with respect to the optically active isomer present in minor amount, and determined by high performance liquid phase chromatography (HPLC) on a chiral stationary phase.

This optical purity can be defined by the equation described on page 107 of the book of J. MARCH, "Advanced Organic Chemistry", John Wiley & Sons, Inc., New York, 3 Edition, 1985:

$$\text{Optical purity (in \%)} = \frac{[(+)] - [(-)]}{[(+)] + [(-)]} \times 100$$

Where [(+)]=concentration of the dextrorotatory enantiomer; and

[(−)]=concentration of the levorotatory enantiomer.

The present invention further relates to a process for preparing the levorotatory and dextrorotatory enantiomers of 1-[(4-chlorophenyl)phenylmethyl] -4-[(4-methylphenyl)sulfonyl]piperazine of formula I, which comprises reacting an enantiomer of (4-chlorophenyl)phenylmethylamine of the formula

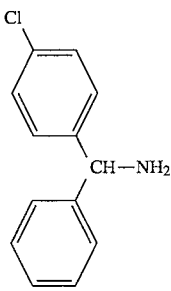

with a N,N-diethyl-4-methylbenzenesulfonamide of the formula

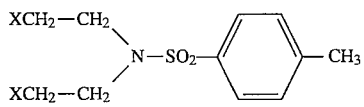

wherein X is a chlorine, bromine or iodine atom or the (4-methylphenyl)sulfonyloxy or methylsulfonyloxy group, in the presence of 2.2 to 4.4 equivalents of an organic or inorganic base per equivalent of the enantiomer of (4-chlorophenyl)phenylmethylamine and at the boiling point of the reaction mixture.

Bases suitable for use to prepare compounds of formula I include organic bases such as ethyldiisopropylamine, N-ethylmorpholine, 2,4,6-trimethylpyridine or triethylamine, preferably ethyldiisopropylamine, and inorganic bases such as sodium carbonate.

The levorotatory and dextrorotatory enantiomers of (4-chlorophenyl)phenylmethylamine of formula II, used as starting materials are known compounds; they can be prepared by chemical resolution of racemic (4-chlorophenyl)phenylmethylamine by known methods using tartaric acid. These enantiomers can be prepared with an optical purity of at least 98%.

The compounds of formula III used as starting materials are also known products which can be easily obtained starting from bis(2-hydroxyethyl)amine and using known methods.

The present invention further relates to the use of the new levorotatory and dextrorotatory enantiomers of 1-[(4-chlorophenyl)phenylmethyl] -4-[(4-methylphenyl)sulfonyl]piperazine of formula I, for the preparation of the substantially optically pure enantiomers of 1-[ (4-chlorophenyl)phenylmethyl]piperazine of the formula

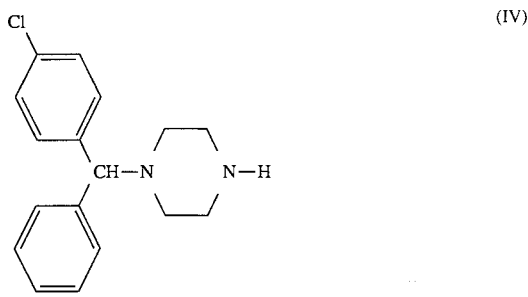

According to the present invention, the levorotatory and dextrorotatory enantiomers of the compound of formula IV are prepared by a process, which comprises subjecting an enantiomer of 1-[(4-chlorophenyl)phenylmethyl]-4-[(4methylphenyl)sulfonyl] piperazine of formula I to hydrolysis with hydrobromic acid, in acetic acid medium and in the presence of a phenolic compound, preferably 4-hydroxybenzoic acid.

This hydrolysis is generally carried out at a temperature of between 18 and 100° C., preferably at a temperature of about 25° C.

The advantages resulting from the use of 1-[(4-chlorophenyl)phenylmethyl] -4-[(4-methylphenyl)sulfonyl]piperazine of formula I, in the form of its levorotatory or dextrorotatory enantiomers according to the invention, are numerous.

These advantages appear not only at the level of the route which leads to the enantiomers of the compound of formula I but also at the level of the conversion step of these enantiomers to prepare the substantially optically pure enantiomers of 1-[(4-chlorophenyl)phenylmethyl]piperazine of formula IV.

First of all, we have found that the enantiomers of the compound of formula I, with a 4-methylphenylsulfonyl group on the amine function, were practically the sole enantiomers of being synthesized in a wholly satisfactory manner. Indeed, if, in the preparation of these compounds, it is attempted to replace the N,N-diethyl-4-methylbenzenesulfonamide of formula III by a corresponding compound, in which the 4-methylphenylsulfonyl group has been replaced by hydrogen or by another protecting group of the amine function such as for example a carbonyl, alkyl or triphenylmethyl group, an important racemization of the starting compound of formula II and/or of the compound of formula I, or the production of .many undesirable by-products, is observed during the formation of the enantiomer of the compound of formula I.

Moreover, the starting materials of formula III, wherein the 4-methylphenylsulfonyl group has been replaced by hydrogen, are known to be extremely toxic due to the presence of a free amine group (nitrogen mustards).

However, all of these significant disadvantages can be avoided by using the N,N-diethyl-4-methylbenzenesulfonamide of formula III, as starting material. Indeed, the enantiomers of 1-[(4-chlorophenyl)phenylmethyl]-4-[(4-methylphenyl)sulfonyl] piperazine of formula I, according to the invention, are prepared by a process which does not cause racemization and provides a high yield, which can reach 89%, and these enantiomers are obtained with an optical purity greater than 98% which, in many cases, approaches 100%, using sulfonated raw materials of relatively low toxicity and much less hazardous to manipulate. This last point means also a considerable advantage as regards the industrial application of the process according to the invention.

Moreover, the use of the enantiomers of the compound of formula I is particularly advantageous for the preparation of the enantiomers of 1-[(4-chlorophenyl)phenylmethyl]piperazine of formula IV. Indeed, on the one hand, the enantiomers of 1-[(4-chlorophenyl)phenylmethyl]piperazine of formula IV are obtained with a yield much greater than 80%. This yield is considerably higher than that achievable using the process described in British patent No. 2,225,321;

on the other hand, since the hydrolysis reaction, leading to the formation of the enantiomers of the compound of formula IV, is non-racemizing, these enantiomers are obtained with an optical purity which is much greater than 95%, even approaching 100%.

The enantiomers of 1-[(4-chlorophenyl)phenylmethyl]-4-[(4-methylphenyl)sulfonyl]piperazine of formula I, according to the invention, thus, open up a highly favorable preparative route to the enantiomers of 1-[(4-chlorophenyl)phenylmethyl]piperazines of the formula IV.

The substantially optically pure levorotatory and dextrorotatory enantiomers of 1-[(4-chlorophenyl)phenylmethyl]piperazine of formula IV, so prepared, are of interest mainly as precursors in the preparation of substantially optically pure therapeutically active levorotatory and dextrorotatory forms of 1-[(4-chlorophenyl)phenylmethyl]piperazines of the formula

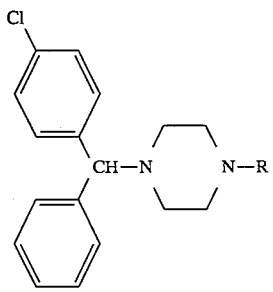

(V)

wherein R is a methyl, (3-methylphenyl)methyl, (4-tert-butylphenyl)methyl, 2-(2-hydroxyethoxy)ethyl, 2-[2-(2-hydroxyethoxy)ethoxy]ethyl, 2-(carbamoylmethoxy) ethyl, 2-(methoxycarbonylmethoxy)ethyl or 2-(carboxymethoxy)ethyl radical.

These compounds, which are already known in the racemic form, possess valuable pharmacological properties and may be used for the treatment of asthma, allergies and inflammation or as sedative, tranquilizing or anxiolytic agents.

The preferred compounds of formula V are the levorotatory and dextrorotatory enantiomers of 1-[(4-chlorophenyl)phenylmethyl]-4-methylpiperazine, of 1-[(4-chlorophenyl)phenylmethyl]-4-[(3-methylphenyl)methyl]piperazine, of 1-[(4-tert-butylphenyl)methyl]-4-[(4-chlorophenyl)phenylmethyl]piperazine, of 2-[2-[4-[(4-chlorophenyl)phenylmethyl]-1-piperazinyl]ethoxy]ethanol, of 2-[2-[2-[4-[(4-chlorophenyl)phenylmethyl]-1-piperazinyl]ethoxy]ethoxy]ethanol, of 2-[2-[4-[(4-chlorophenyl)phenylmethyl]-1-piperazinyl]ethoxy]acetamide, of methyl 2-[2-[4-[(4-chlorophenyl)phenylmethyl]-1-piperazinyl]ethoxy]acetate and of 2-[2-[4-[(4-chlorophenyl)phenylmethyl]-1-piperazinyl]ethoxy]acetic acid and the pharmaceutically acceptable salts of these enantiomers.

The preparation of these substantially optically pure enantiomers can be carried out by means of known methods which comprise reacting an enantiomer of the compound of formula IV, while hot, with a halide of the formula RX wherein R has the meaning given above and X represents a halogen atom. The enantiomers of formula V are new compounds, with the exception of the compounds where R is a 2-(carboxymethoxy) ethyl radical, and possess valuable antihistaminic properties; in particular, they exhibit a very distinct difference in behavior as regards the inhibition of the histamine $H_1$ receptor, one of the enantiomers being a competitive inhibitor and the other a non-competitive inhibitor.

The pharmacological tests described below demonstrate these properties.

The following Examples illustrate the invention without, however, limiting it. In these Examples, the melting points are determined by differential scanning calorimetry (D.S.C.) with a temperature gradient of 20° C./min. The optical purity as defined hereinbefore was determined by high performance liquid phase chromatography, on a chiral stationary phase (CHIRALPAK AD column, 250×4.6 mm; eluent: 50:50:0.1 (v/v/v) mixture of hexane-ethanol-diethylamine; pressure 104 bar; temperature 25° C.; flow rate 1 ml/min).

Example 1. Preparation of the levorotatory and dextrorotatory enantiomers of (4-chlorophenyl)phenylmethylamine of formula II.

1. Levorotatory (−)-(4-chlorophenyl)phenylmethylamine.

This compound is prepared by resolution of racemic (4-chlorophenyl)phenylmethylamine by means of (+)-tartaric acid according to the method described by R. CLEMO et al. (J. Chem. Soc., (1939), p. 1958–1960).

2. Dextrorotatory (+)-(4-chlorophenyl)phenylmethylamine.

This compound is prepared by resolution of racemic (4-chlorophenyl)phenylmethylamine by means of (−)-tartaric acid according to the method described by R. CLEMO et al. (loc.cit.).

3. Recovery of the unrequired enantiomer of (4-chlorophenyl)phenylmethylamine.

With the aim of recovering and recycling the unrequired enantiomer of (4-chlorophenyl)phenylmethylamine, the compound is subjected to a racemization reaction and the resulting racemic (4-chlorophenyl)phenylmethylamine is then subjected to a new step of resolution by means of an isomer of tartaric acid according to the method described at point 1 or 2 above.

4.35 g (0.02 mole) of dextrorotatory (+)-(4-chlorophenyl)phenylmethylamine, 244 mg (0.002 mole) of 2-hydroxybenzaldehyde and 1.1 g (0.02 mole) of sodium methoxide are suspended in 21.8 ml of methanol. The mixture is heated under reflux for five and a half hours, then allowed to return to ambient temperature and 6.7 ml of concentrated hydrochloric acid are added dropwise to the mixture. The methanol is evaporated, the residue taken up in 50 ml of water, and a further 25 ml of concentrated hydrochloric acid are added thereto. After 1 hour, the white precipitate which forms is filtered off, washed with water and dried under vacuum at 40° C. 3.7 g of racemic (4-chlorophenyl)phenylmethylamine are obtained. Yield: 73%. $[\alpha]_D^{25}$: 0° (c=1, methanol).

Example 2. Preparation of N,N-diethyl-4-methylbenzenesulfonamides of formula III.

1. 4-methyl-N,N-bis[2-[(4-methylphenyl)sulfonyloxy]ethyl]benzenesulfonamide. (formula III, X=(4-methylphenyl)sulfonyloxy).

This compound is prepared from N,N-bis(2-hydroxyethyl)-4-methylbenzenesulfonamide according to the method described by D. H. PEACOCK and U.C. DUTTA (J. Chem. Soc., (1934) p. 1303–1305).

M.P. : 75.9° C. Yield: 79.7%.

2. 4-methyl-N,N-bis[2-(methylsulfonyloxy)ethyl]benzenesulfonamide.

(formula III, X=methylsulfonyloxy).

A solution of 11.4 g (0.1 mole) of methanesulfonyl chloride in 17.1 ml of dichloromethane is cooled to 5° C. A solution of 13 g (0.05 mole) of N,N-bis( 2-hydroxyethyl)-4-methylbenzenesulfonamide and 10.1 g (0.1 mole) of triethylamine in 52 ml of dichloromethane is then added dropwise with stirring. The resulting mixture is allowed to return to ambient temperature and stirred for a further 3 hours. The reaction mixture is then extracted three times with 40 ml water. The organic phase is dried over sodium sulfate, filtered and concentrated in a rotating evaporator. The resulting oil is then crystallized from ethanol. 17.8 g of 4-methyl-N,N-bis[2-methylsulfonyloxy) ethyl]benzenesulfonamide are obtained.

M.P. : 64.6° C. Yield : 85.7%.

3. N,N-bis(2-chloroethyl)-4-methylbenzenesulfonamide. (formula III, X = Cl),

This compound is prepared using the method described by K. A. AL-RASHOOD et al. (Arzneim.-Forsch./Drug Res. 40(II) (1990), p.1242–1245).

M.P. : 45.8° C. Yield: 69.0%.

4. N,N-bis(2-iodoethyl)-4-methylbenzenesulfonamide. (formula III, X=I).

5.7 g (0.01 mole) of 4-methyl-N,N-bis[2-[(4-methylphenyl) sulfonyloxy]ethyl]benzenesulfonamide (prepared as indicated in 1 above) are dissolved in 57 ml of acetone and 4.5 g (0.03 mole) of sodium iodide are added thereto. The resulting mixture is heated under reflux for 22 hours. It is then allowed to cool and the acetone is evaporated off. The solid residue is taken up in a mixture of 10 ml of water and 25 ml of dichloromethane and the two phases are separated. The aqueous phase is extracted with 25 ml of dichloromethane and the organic phases are combined. The combined organic phase is washed successively with 10 ml of a 10% aqueous solution of sodium thiosulfate and then with 10 ml of water. The organic phase is then dried over sodium sulfate, filtered and evaporated. The white solid obtained is dried under vacuum at 25° C. 4.7 g of N,N-bis(2-iodoethyl)-4-methylbenzenesulfonamide are obtained.

M.P. 93.8° C. Yield: 98%.

5. N,N-bis(2-bromoethyl)-4-methylbenzenesulfonamide. (formula III, X=Br)

This compound is prepared using the method described at point 4 above, except that sodium bromide is used in place of sodium iodide and the reaction mixture is heated in acetone under reflux for 16 days.

M.P. : 69.2° C. Yield 98.7%.

Example 3. Preparation of enantiomers of 1-[(4-chlorophenyl)phenylmethyl]-4-[(4-methylphenyl) sulfonyl]piperazine of formula I.

A1. Levorotatory (−)-1-[(4-chlorophenyl)phenylmethyl]-4-[(4-methylphenyl)sulfonyl]piperazine.

3.4 g (0.0156 mole) of levorotatory (-)-(4-chlorophenyl)phenylmethylamine (prepared in Example 1.1) and 5.1 g (0.0172 mole) of N,N-bis(2-chloroethyl)-4-methylbenzenesulfonamide (prepared in Example 2.3) in 6 ml (4.4 g or 0.0343 mole) of ethyldiisopropylamine are mixed in a 25 ml round-bottomed flask. The mixture is heated under reflux (127° C.) for 4 hours and then cooled, with stirring, to 86° C. and 13.8 ml of methanol are added at once. The mixture is then cooled in an ice bath and still stirred for 1 hour. The precipitate which forms is filtered off, washed with 10 ml of methanol and dried under vacuum at 40° C. The product is recrystallized from a 3:1 (v/v) mixture of methanol and acetone. 6 g of levorotatory (−)-1-[(4-chlorophenyl)phenylmethyl]-4-[(4-methylphenyl)sulfonyl]piperazine are obtained.

M.P. 171.1° C. Yield : 87.2%.

$[\alpha]_D^{25}$:−40.68° (c=1, toluene)

Optical purity: 100%

Analysis for $C_{24}H_{25}ClN_2O_2S$ in %:

Calc. : C 65.37 H 5.71 N 6.35 Cl 8.04 S 7.27

Found : 65.95 5.80 6.60 8.12 7.33

A2 to A5. Influence of the nature of the base.

Levorotatory (−)-1-[(4-chlorophenyl)phenylmethyl]-4-[(4-methylphenyl)sulfonyl]piperazine is also prepared from N,N-bis(2-chloroethyl)-4-methylbenzenesulfonamide using the method described at point A1 above, but with various other bases in place of ethyldiisopropylamine.

The results obtained are set out in Table I, wherein the first column indicates the number of the Example, the second column, the base used, the third column, the amount of base used, expressed in equivalents per equivalent of (−)-(4-chlorophenyl)phenylmethylamine, the fourth column, the time (in hours) during which the reaction mixture is kept under reflux, the fifth column, the yield of levorotatory (−)-1-[(4-chlorophenyl)phenylmethyl]-4-[(4-methylphenyl) sulfonyl] piperazine obtained and the sixth column, the optical purity of the product obtained, expressed in percent.

TABLE I

| Example 3 | Base | Amount of base (eq.) | Time (hours) | Yield (%) | Optical Purity (%) |
|---|---|---|---|---|---|
| A1 | ethyldiisopropylamine | 2.2 | 4 | 87.2 | ≈100 |
| A2 | 2,4,6-trimethylpyridine | 3.0 | 1.5 | 64.2 | ≈100 |
| A3 | N-ethylmorpholine | 2.2 | 4 | 61.2 | 98.4 |
| A4 | triethylamine | 3.0 | 48 | 59.7 | ≈100 |
| A5 | $Na_2CO_3$/xylene* | 3.0 | 28 | 56.7 | ≈100 |

*Auxiliary solvent for reaction

From this Table, it can be seen that the nature of the base has only a small influence on the optical purity of the product obtained. However, it appears that ethyldiisopropylamine is much more advantageous as regards the yield of the reaction.

A6 to A9. Influence of the nature of the N,N-diethyl-4-methylbenzenesulfenamide of formula III.

Levorotatory (−)-1-[(4-chlorophenyl)phenylmethyl]-4-[(4-methylphenyl)sulfonyl] piperazine is also prepared using the method described at point A1 above, but the N,N-bis(2-chloroethyl)-4-methylbenzenesulfonamide of formula III (X=Cl) used as starting material is replaced by the corresponding brominated (X=Br), iodinated (X=I), tosylated (X=(4-methylphenyl)sulfonyloxy) or mesylated (X=methylsulfonyloxy) derivative, prepared respectively-in Examples 2.5, 2.4, 2.1 and 2.2.

In Table II, the first column gives the number of the Example, the second column, the nature of the substituent X in the starting material of formula III, the third column, the amount of the compound of formula III used, expressed in equivalents per equivalent of (−)-(4-chlorophenyl)phenylmethylamine, the fourth column, the time, expressed in hours during which the reaction mixture is kept under reflux, the fifth column, the yield of levorotatory (−)-1-[(4chlorophenyl)phenylmethyl]-4-[(4-methylphenyl) sulfonyl] piperazine obtained and the sixth column, the optical purity of the product expressed in percent.

TABLE II

| Example 3 | Compound of formula III Substituent X | Amount of III (eq.) | Time (hours) | Yield (%) | Optical Purity (%) |
| --- | --- | --- | --- | --- | --- |
| A1 | Cl | 1.1 | 4 | 87.2 | ≈100 |
| A6 | Br | 1 | 1 | 88.9 | ≈100 |
| A7 | methylsulfonyloxy | 1 | 2 | 84.6 | ≈100 |
| A8 | I | 1 | 1 | 84.1 | 99.4 |
| A9 | (4-methylphenyl)sulfonyloxy | 1 | 1 | 83.8 | ≈100 |

From this Table, it can be seen that the nature of the compound of formula III has only a small influence on the optical purity of the product obtained. Moreover, the compound of formula III has only a very small influence on the yield of the reaction, although the best yield is obtained using the bromine derivative.

B. Dextrorotatory
(+)-1-[(4-chlorophenyl)phenylmethyl]-4-[(4-methylphenyl)sulfonyl]piperazine.

57 g (0.2618 mole) of dextrorotatory (+)-(4-chlorophenyl)phenylmethylamine (prepared in Example 1.2) and 86.4 g (0.2917 mole) of N,N-bis(2-chloroethyl)-4-methylbenzenesulfonamide (prepared in Example 2.3) are added to 200 ml (1.15 mole) of ethyldiisopropylamine in a 500 ml three-necked round-bottomed flask. The mixture is heated under reflux for 3 hours, then poured in 400 ml of methanol and the mixture is cooled, in an ice bath, and stirred for 1 hour. The precipitate which forms is filtered off, washed with methanol and dried under vacuum at 50° C. 88.6 g of dextrorotatory (+)-1-[(4-chlorophenyl)phenylmethyl]-4-[(4-methylphenyl)sulfonyl]piperazine are obtained.

M.P. 173.3° C. Yield: 76.7%.

$[\alpha]_D^{25}$: +43.2° (c=0.5, toluene).

Optical purity: 98.35%.

Analysis for $C_{24}H_{25}ClN_2O_2S$ in %:

Calc. : C 65.38 H 5.71 N 6.35 C 8.04 S 7.27

Found: 64.98 5.70 6.40 7.96 7.35

Example 4. Preparation of levorotatory and dextrorotatory enantiomers of 1-[(4-chlorophenyl)phenylmethyl] piperazine of formula IV.

1. Levorotatory (−)-1-[(4-chlorophenyl)phenylmethyl] piperazine.

370 g (0.839 mole) of levorotatory (−)-1-[(4-chlorophenyl)phenylmethyl] -4-[(4-methylphenyl)sulfonyl]piperazine (prepared in Example 3.A1) and 405 g of 4-hydroxybenzoic acid are added to 1 liter of a 30% solution of hydrobromic acid in acetic acid. The suspension is stirred for 17 hours at 25° C. 2 liters of water are then added thereto and the suspension is cooled in an ice bath. The precipitate which forms is filtered and washed with 750 ml of water. 2 liters of toluene and 0.9 liters of a 50% aqueous solution of sodium hydroxide are then added to the filtrate. The organic phase is decanted off and washed with 100 ml of water and then once again with 1 liter of a saturated aqueous solution of sodium chloride. The organic phase is dried over sodium sulfate, filtered and the solvent evaporated off under reduced pressure. The residue is recrystallized from 600 ml of boiling hexane. The solution is filtered while hot, so as to remove any slightly insoluble material and the filtrate is then allowed to crystallize, first at ambient temperature, and then for 24 hours in an ice bath. The crystals are filtered off, washed with hexane and dried under vacuum at 40° C. 204.15 g of levorotatory (−)-1-[(4chlorophenyl) phenylmethyl]piperazine are obtained.

M.P. : 90.5° C. Yield: 84.8%.

$[\alpha]_D^{25}$: 90.5° C. (c=1, methanol).

Optical purity : ≧99.8%.

Analysis for $C_{17}H_{19}ClN_2$ in % :

Calc.: C 71.19 H 6.68 N 9.77 Cl 12.36

Found: 71.19 6.84 9.55 11.48

2. Dextrorotatory (+)-1-[(4-chlorophenyl)phenylmethyl] piperazine.

Dextrorotatory (+)-1-[(4-chlorophenyl)phenylmethyl] piperazine is prepared using the method described at point 1 above, but the starting levorotatory enantiomer of 1-[(4-chlorophenyl)phenylmethyl]-4-[(4-methylphenyl)sulfonyl] piperazine is replaced by the dextrorotatory enantiomer (prepared in Example 3.B).

M.P. : 91.5° C. Yield: 97.9%.

$[\alpha]_D^{25}$: +14.94° (c=1, methanol).

Optical purity: 100%.

Analysis for $C_{17}H_{19}ClN_2$ in % :

Calc. : C 71.19 H 6.68 N 9.77 Cl 12.36

Found: 70.90 6.74 9.72 12.23

Example 5. Use of the enantiomers of 1-[(4-chlorophenyl)phenylmethyl]piperazine in the preparation of therapeutically active compounds of formula V.

1. Levorotatory dihydrochloride of 1-[(4-chlorophenyl)phenylmethyl]4-[(3-methylphenyl)methyl] piperazine.

A solution containing 10 g (0.0348 mole) of dextrorotatory (+)-1-[(4-chlorophenyl)phenylmethyl]piperazine (prepared in Example 4.2) in 100 ml of n-butanol is heated at 50° C. 5.5 ml (0.0417 mole) of 1-chloromethyl-3-methylbenzene, 8.9 g (0.0836 mole) of sodium carbonate and 0.5 g (0.0030 mole) of potassium iodide are added thereto and the mixture is heated at reflux temperature for 3 hours. The mixture is then cooled and the solid residues removed by filtration and washed with 200 ml of toluene. The organic phases are combined and the solvents evaporated until a residual oil is obtained. The oil is redissolved in 500 ml of ethanol to which 15 ml of concentrated hydrochloric acid, dissolved in 35 ml of ethanol, are added. This solution is cooled in an ice bath, the resulting precipitate filtered off and the filtrate evaporated. The residue obtained after evaporation and the precipitate are combined and suspended in 100 ml of isopropyl alcohol. The suspension is filtered and the solids are washed with a small amount of isopropyl alcohol and dried under vacuum at 50° C.

12.7 g of the levorotatory dihydrochloride of 1-[(4-chlorophenyl)phenylmethyl] -4-[(3-methylphenyl)methyl] piperazine are obtained.
M.P. : 252.3° C. Yield : 78.6%.
$[\alpha]_{365}^{25}$: −27.96° (c=1, methanol).
Optical purity: ≈100%.
Analysis for $C_{25}H_{27}ClN_2.2HCl$ in % :
Calc. : C 64.73 H 6.30 N 6.04 Cl⁻15.29
Found : 64.45 6.42 5.93 15.18

2. Dextrorotatory dihydrochloride of 1-[(4-chlorophenyl)phenylmethyl]-4-[ (3-methylphenyl)methyl]piperazine.

The procedure described at point 1 above is followed using the levorotatory 1-[(4-chlorophenyl)phenylmethyl] piperazine (prepared in Example 4.1) in place of the dextrorotatory enantiomer and using the same quantities of reagents. 13 g of the dextrorotatory dihydrochloride of 1-[(4-chlorophenyl)phenylmethyl] -4-[(3-methylphenyl)methyl]piperazine are obtained.
M.P.: 252.9° C. Yield: 80.4%.
$[\alpha]_{365}^{25}$: +27.5° (c=1, methanol).
Optical purity: ≈100%.
Analysis for $C_{25}H_{27}ClN_2.2HCl$ in %:
Calc. : C 64.73 H 6.30 N 6.04 Cl⁻15.29
Found: 64.47 6.92 5.88 15.18

3. Levorotatory dihydrochloride of 1-[(4-tert-butylphenyl)methyl]-4-[(4-chlorophenyl)phenylmethyl] piperazine A solution containing 10 g (0.0348 mole) of dextrorotatory (+)-1-[(4-chlorophenyl)phenylmethyl] piperazine (prepared in Example 4.2) in 100 ml of n-butanol is heated to 50° C. 7.6 ml (0.0418 mole) of 1-chloromethyl-4-tertbutylbenzene, 8.9 g (0.0836 mole) of sodium carbonate and 0.5 g (0.0030 mole) of potassium iodide are added thereto and the mixture is heated at reflux temperature for 1 hour. It is then cooled and the solids are removed by filtration and washed with 200 ml of toluene. The organic phases are combined and the solvents evaporated until a residual oil is obtained. This oil is redissolved in 300 ml of acetone, and 15 ml of concentrated hydrochloric acid, dissolved in 35 ml of acetone, are added thereto, followed by a further 200 ml of acetone, The mixture is cooled in an ice bath and the precipitate which forms is filtered off and dried under vacuum at 50° C. 14.68 g of the levorotatory dihydrochloride of 1-[(4-tertbutylphenyl)methyl] -4-[(4-chlorophenyl)phenylmethyl]piperazine are obtained.
M.P. : 257.7° C. Yield: 83.3%.
$[\alpha]_{365}^{25}$ : −13.26° (c=0.2, methanol).
Optical purity: ≈100%.
Analysis for $C_{28}H_{33}ClN_2.2HCl$ in %:
Calc. : C 66.47 H 6.97 N 5.54 Cl 14.01
Found : 66.35 7.39 5.45 13.85

4. Dextrorotatory dihydrochloride of 1-[(4-tert-butylphenyl)methyl]-4-[(4-chlorophenyl)phenylmethyl] piperazine.

This compound is prepared by using the method described at point 3 above, but starting with 4 g of levorotatory (−)-1-[(4-chlorophenyl)phenylmethyl] piperazine (prepared in Example 4.1). 4.75 of the dextrorotatory dihydrochloride of 1-[(4-tert-butylphenyl)methyl]-4-[(4-chlorophenyl)phenylmethyl] piperazine are obtained.
M.P. : 273.9° C. Yield: 67.4%.
$[\alpha]_{365}^{25}$ : +11.33° (c=b 0.2 methanol).
Optical purity: ≈100%.
Analysis for $C_{28}H_{33}ClN_2.2HCl$ in %:
Calc. : C 66.47 H 6.97 N 5.54 Cl⁻ 14.01
Found: 66.37 7.16 5.27 13.85

5. Levorotatory dihydrochloride of 2-[2-[4-[(4-chlorophenyl) phenylmethyl]-1-piperazinyl]ethoxy]ethanol.

A solution containing 10 g (0.0348 mole) of dextrorotatory (+)-1.[(4-chlorophenyl)phenylmethyl]piperazine (prepared in Example 4.2) in 100 ml of n-butanol is heated to 50° C. 5 ml (0.0464 mole) of 2-(2-chloroethoxy) ethanol, 8.9 g (0.0836 mole) of sodium carbonate and 0.5 g (0.0030 mole) of potassium iodide are added thereto and the mixture is heated at reflux temperature for 16 hours. A further 2 ml of 2-(2-chloroethoxy) ethanol are added and refluxing is continued for a further 4 hours. The mixture is cooled and filtered and the precipitate washed with 200 ml of toluene. The organic phases are evaporated until an oil is obtained and this is dissolved in 100 ml of ethanol. 12 ml of concentrated hydrochloric acid, dissolved in 38 ml of ethanol, are added thereto. The solvent is evaporated and the residue recrystallized from ethanol. The precipitate is filtered off and washed with a small amount of isopropyl alcohol (first crop). The filtrate is evaporated and the solid residue washed with a small amount of isopropyl alcohol (second crop). The two crops are recrystallized together from a 30:1 (v/v) mixture of isopropyl alcohol and methanol. 10.57 g of the levorotatory dihydrochloride of 2-[2-[4-[(4-chlorophenyl)phenylmethyl] -1-piperazinyl]ethoxy]ethanol are obtained.
M.P. : 229.8° C. Yield: 67.8%.
$[\alpha]_{365}^{25}$ : −6.07° (c=1, water).
Optical purity : ≈100%.
Analysis for $C_{21}H_{27}ClN_2O_2.2HCl$ in %
Calc. : C 56.32 H 6.53 N 6.26 Cl⁻ 15.83
Found : 56.32 6.79 6.08 15.63

6. Dextrorotatory dihydrochloride of 2-[2-[4-[(4-chlorophenyl) phenylmethyl]-1-piperazinyl]ethoxy]ethanol.

Using the same amounts of reagents as used in the method described at point 5 above, the dextrorotatory enantiomer is prepared in the same way, but starting with levorotatory (−)-1-[(4-chlorophenyl)phenylmethyl]piperazine (prepared in Example 4.1). 11.7 g of the dextrorotatory dihydrochloride of 2-[2-[4-[(4-chlorophenyl)phenylmethyl]-1-piperazinyl]ethoxy]ethanol are obtained.
M.P. : 231.3° C. Yield : 70.5%.
$[\alpha]_{365}^{25}$ : 5.16° (c=1, water).
Optical purity : ≈100%.
Analysis for $C_{21}H_{27}ClN_2O_2.2HCl$ in %
Calc. : C 56.32 H 6.52 N 6.25 Cl⁻ 15.83
Found : 55.75 6.54 6.10 15.81

7. Levorotatory dihydrochloride of 2-[2-[2-[4-[(4-chlorophenyl) phenylmethyl]-1-piperazinyl]ethoxy]ethoxy] ethanol.

A solution containing 10 g (0.0348 mole) of dextrorotatory (+)-1-[(4-chlorophenyl)phenylmethyl] piperazine (prepared in Example 4.2) in 100 ml of n-butanol is heated to 40° C. 6.1 ml (0.0419 mole) of 2-[2-(2-chloroethoxy)ethoxy] ethanol, 8.9 g (0.0836 mole) of sodium carbonate and 0.5 g (0.0030 mole) of potassium iodide are added thereto. The mixture is heated at reflux temperature for six hours. It is then cooled and the solids are removed by filtration and washed with a small amount of toluene. The filtrate and the washing solvent are combined and the solvents evaporated. The residue is taken up in 50 ml of toluene which is then evaporated. The residue obtained is taken up again in 100 ml of toluene, washed with a 100 ml of water and the organic phase! evaporated. The oil obtained after evaporation is dissolved in 100 ml of isopropyl alcohol. A solution containing 12 ml of concentrated hydrochloric acid in 38 ml of isopropyl alcohol is added thereto and the solvent evaporated. The solid residue is taken up in 150 ml of hot isopropyl alcohol, 100 ml of hexane are added and the solution heated under reflux. The solution is then cooled in an ice bath, filtered and the precipitate is washed with 50 ml of a 1:1 (v/v) mixture of isopropyl alcohol and hexane and then with 50 ml of hexane. The resulting solid product is dried under vacuum at 50° C. 12.2 g of the levorotatory dihydrochloride of 2-[2-[2-[4-[(4-chlorophenyl)phenylmethyl]-1-piperazinyl] ethoxy]ethoxy]ethanol are obtained.

M.P.: 198° C. Yield : 71.13%.
$[\alpha]_{365}^{25}$: $-10.7°$ (c=1, methanol)
Optical purity : ≈100%.
Analysis for $C_{23}H_{31}ClN_2O_3 \cdot 2HCl$ in % :
Calc. : C 56.16 H 6.76 N 5.69 $Cl_{tot}$ 21.62
Found: 56.34 7.00 5.67 21.76

8. Dextrorotatory dihydrochloride of 2-[2-[2-[4-[(4-chlorophenyl) phenylmethyl]-1-piperazinyl]ethoxy]ethoxy] ethanol.

Using the same method as described at point 7 above, the dextrorotatory enantiomer is prepared starting from levorotatory (−)-1-[(4-chlorophenyl)phenylmethyl] piperazine (prepared in Example 4.1).

M.P. : 196.1° C. Yield 73.8%.
$[\alpha]_{365}^{25}$: $+8.94°$ (c=1 methanol).
Optical purity : ≈100%.
Analysis for $C_{23}H_{31}ClN_2O_3 \cdot 2HCl$ in % :
Calc. : C 56.16 H 6.76 N 5.69 $Cl_{tot}$ 21.62
Found: 56.48 6.96 5.65 22.1

9. Levorotatory (−)-2-[2-[4-[(4-chlorophenyl)phenylmethyl]-1-piperazinyl]ethoxy ]acetamide.

77 g (0.2685 mole) of levorotatory (−)-1-[(4-chlorophenyl)phenylmethyl] piperazine (prepared in Example 4.1), 40.5 g (0.2932 mole) of 2-(2-chloroethoxy)acetamide, 62.8 g (0.591 mole) of sodium carbonate and 2 g (0.0120 mole) of potassium iodide are added to 700 ml of toluene. The mixture is heated at reflux temperature for 24 hours. 10 g of Norit are then added and the mixture is filtered while hot through Dicalite. The filtrate is washed with 500 ml of water and then with 500 ml of a saturated aqueous solution Of sodium chloride. The organic phase is separated and dried over 250 g of sodium sulfate. It is then filtered and the solvent is evaporated. The residual oil is taken up in 1500 ml of hot diisopropyl oxide. The solution is heated under reflux and allowed to crystallize by cooling in an ice bath. The crystals are filtered, washed with a small amount of diisopropyl oxide and dried under vacuum at 40° C. 82.91 g of levorotatory (−)-2-[2-[4-[(4-chlorophenyl)phenylmethyl]-1-piperazinyl]ethoxy] acetamide are obtained.

M.P. : 94.3° C. Yield: 79.6%.
$[\alpha]_{365}^{25}$ : $-23.5°$ (c=1 methanol).

Optical purity : ≈100%.
Analysis for $C_{21}H_{26}ClN_3O_2$ in % :
Calc. : C 65.02 H 6.76 N 10.83 Cl 9.14
Found: 65.39 6.70 10.99 9.23

10. Dextrorotatory (+)-2-[2-[4-[(4-chlorophenyl)phenylmethyl]-1-piperazinyl ]ethoxy]acetamide.

15 g (0.0523 mole) of dextrorotatory (+)-1-[(4-chlorophenyl)phenylmethyl] piperazine (prepared in Example 4.2), 8.3 g (0.0601 mole) of 2-(2-chloroethoxy)acetamide, 12.8 g (0.1203 mole) of sodium carbonate and 0.5 g (0.0030 mole) of potassium iodide are added to a mixture of 100 ml of p-xylene and 150 ml of toluene. The mixture is heated at reflux temperature for 17 hours. A small amount of Norit is added and the mixture is filtered while hot through Dicalite. The residue on the filter is washed with a small amount of toluene and the filtrate and washing solution are combined. The solvents are evaporated and the residue is taken up in 100 ml of toluene. The organic phase is washed successively with 100 ml of water and twice with 100 ml of a saturated aqueous solution of sodium chloride. The organic phase is separated off and the solvent evaporated. At this point, the crude residue obtained could be purified in a manner similar to that described at point 9 above, in order to obtain dextrorotatory (+)-2-[2-[ 4-[(4-chlorophenyl)phenylmethyl]-1-piperazinyl]ethoxy]acetamide in the form of the free base. However, if desired, the crude residue may also be converted to the corresponding dihydrochloride in the following manner : the crude residue obtained is taken up in 100 ml of acetone, cooled in an ice bath and 15 ml of concentrated hydrochloric acid are added dropwise thereto. A further 200 ml of acetone are added and the mixture is cooled and stirred on an ice bath for 1 hour. The precipitate is filtered off and dried under vacuum at 50° C. 19 g of the levorotatory dihydrochloride of 2-[2-[4-[(4-chlorophenyl) phenylmethyl-1-piperazinyl]ethoxy]acetamide are obtained.

M.P. : 237.4° C. Yield 78.8%.
$[\alpha]_{365}^{25}$ : $-19.64°$ (c=1, methanol).
Optical purity : ≈100%.
Analysis for $C_{21}H_{26}ClN_3O_2 \cdot 2HCl$ in % :
Calc.: C 54.73 H 6.12 N 9.12 $Cl_{tot}$ 23.08 Cl⁻ 15.38
Found : 53.70 6.20 8.91 23.08 15.61

11. Levorotatory dimaleate of methyl 2-[2-[4-[(4-chlorophenyl)phenylmethyl ]-1-piperazinyl]ethoxy]acetate.

46 g (0.16 mole) of levorotatory (-)-1-[(4-chlorophenyl)phenylmethyl] piperazine (prepared in Example 4.1), 36.6 g (0.24 mole) of methyl (2-chloroethoxy)acetate, 37.3 g (0.35 mole) of anhydrous sodium carbonate and 1.05 g (0.0064 mole) of potassium iodide are suspended in 46 ml of toluene. The suspension is heated with stirring for 18 hours at reflux temperature, then cooled to ambient temperature and filtered. The solids are washed with 100 ml of toluene and the filtrate and the washing solvent are combined. The toluene is evaporated at 50° C. under reduced pressure in a rotating evaporator. 76 g of a brown oil are obtained and are taken up in 80 ml of dichloromethane. The solution is purified by chromatography (silica column (15 to 40 μm) 1 kg; eluent: pure dichloromethane gradually diluted with methanol up to a maximum of 2% of methanol (v/v)). 43.5 g of methyl 2-[2-[4-[(4-chlorophenyl)phenylmethyl]-1-piperazinyl] ethoxy]acetate in the form of an oil are thus obtained. Yield : 67.5%.

This compound can be converted to the corresponding dimaleate in the following manner: 15 g (0.037 mole) of methyl 2-[2-[4-[(4-chlorophenyl)phenylmethyl]-1-piperazinyl]ethoxy]acetate prepared above are dissolved in 45 ml of methanol at reflux temperature and 9,1 g (0.078 mole) of maleic acid are then added at once thereto. The mixture is maintained at reflux temperature until the maleic acid is completely dissolved, then the solution is allowed to return to ambient temperature, always with stirring. The crystals which form are filtered off and suspended in 15 ml of methanol. The suspension is stirred for an hour and a half at ambient temperature and then again for an hour and a half at 0° C. The crystals are filtered off, washed with 15 ml of methanol at 0° C. and dried to constant weight. 19.5 g of the levorotatory dimaleate of methyl 2-[2-[4-[(4-chlorophenyl)phenylmethyl]- 1-piperazinyl]ethoxy]acetate are obtained.

M.P. 143.5° C. Yield: 56%.
$[\alpha]_{365}^{25}$ : −10.09° (c=1, methanol).
Optical purity : ≈100%.
Analysis for $C_{22}H_{27}ClN_2O_3 \cdot 2C_4H_4O_4$ in % :
Calc. : C 56.79 H 5.56 N 4.41
Found : 56.81 5.68 4.12

12. Dextrorotatory dimaleate of methyl 2-[2-[4-[(4-chlorophenyl)phenylmethyl]-1-piperazinyl] ethoxy]acetate.

14.3 g (0.05 mole) of dextrorotatory (+)-1-[(4-chlorophenyl)phenylmethyl] piperazine (prepared in Example 4.2), 8.4 g (0.055 mole) of methyl (2-chloroethoxy)acetate, 11.7 g (0.11 mole) of anhydrous sodium carbonate and 0.332 g (0.002 mole) of potassium iodide are suspended in 14.3 ml of toluene. The suspension is heated with stirring for 17 hours at reflux temperature. A further 1.52 g (0.01 mole) of methyl (2-chloroethoxy)acetate are added and the suspension is further heated with stirring for 3 hours at reflux temperature, then cooled to ambient temperature and filtered. The solids are washed with 50 ml of toluene and the filtrate and the washing solvent are combined. The toluene is evaporated at 50° C. under reduced pressure in a rotating evaporator. 22.8 g of a brown oil are obtained and are taken up in 45 ml of dichloromethane. The solution is purified by chromatography (silica column (15 to 40 μm) 1 kg; eluent: pure dichloromethane gradually diluted with methanol up to a maximum of 2% of methanol (v/v)). 11.1 g of methyl 2-[2-[4-[(4-chlorophenyl)phenylmethyl]-1-piperazinyl]ethoxy]acetate in the form of an oil are obtained.

Yield : 55.1%.

This compound can be converted to the corresponding dimaleate in the following manner: 8 g (0.0198mole) of methyl 2-[2-[4-[(4-chlorophenyl)phenylmethyl] -1-piperazinyl]ethoxy]acetate prepared above are dissolved in 16 ml of methanol at reflux temperature and 4.85 g (0.0417 mole) of maleic acid are then added at once thereto. The mixture is maintained at reflux temperature until the maleic acid is completely dissolved, then the solution is allowed to return to ambient temperature, always with stirring. The crystals which form are filtered off and suspended in 16 ml of methanol. The suspension is stirred for two hours at ambient temperature. The crystals are filtered off, washed with 10 ml of methanol and dried to constant weight. 7.3 g of the dextrorotatory dimaleate of methyl 2-[2-[4-[(4-chlorophenyl)phenylmethyl] -1-piperazinyl]ethoxy]acetate are obtained.

M.P. 143.2° C. Yield : 32%.
$[\alpha]_{365}^{25}$ : +9.8° (c=1, methanol).
Optical purity : ≈100%.
Analysis for $C_{22}H_{27}ClN_2O_3 \cdot 2C_4H_4O_4$ in % :
Calc. : C 56.79 H 5.56 N 4.41
Found : 56.71 5.58 4.17

13. Levorotatory dihydrochloride of 2-[2-[4-[(4-chlorophenyl)phenylmethyl]-1-piperazinyl ]ethoxy]acetic acid.

26 ml of concentrated hydrochloric acid are added dropwise to a suspension of 25.2 g (0.065 mole) of dextrorotatory (+)-2-[2-[4-[(4-chlorophenyl)phenylmethyl] -1-piperazinyl] ethoxy]acetamide (prepared at point 10 above) in 70 ml of water, causing the temperature of the mixture to rise to 38° C. The mixture is the heated at 50° C. for 17 hours. The reaction mixture is then cooled in an ice bath and the pH brought to a value of between 4 and 5 by addition of a 4N aqueous solution of sodium hydroxide. The resulting solution is extracted successively with 100 ml, then twice with 50 ml of dichloromethane. The organic phases are combined and dried over magnesium sulfate. They are filtered and the solvent is evaporated. The residual oil is dissolved in 243 ml of acetone and the solution is treated with 3.5 g of Norit and filtered through Celite, which is then washed with 35 ml of acetone. The solution is heated at reflux temperature and 198 ml (0.13 mole) of concentrated hydrochloric acid are added dropwise thereto. The mixture is cooled in an ice bath and allowed to stand for one hour. The precipitate which forms is filtered off, washed with 100 ml of acetone and dried under vacuum at 50° C. 24.1 g of the levorotatory dihydrochloride of 2-[ 2-[4-[(4-chlorophenyl)phenylmethyl]-1-piperazinyl]ethoxy]acetic acid are obtained.

M.P. : 229.3° C. Yield : 80.3%.
$[\alpha]_D^{25}$ : −12.79° (c=1 water).
Optical purity : ≈100%.
Analysis for $C_{21}H_{25}ClN_2O_3 \cdot 2HCl$ in %
Calc. : C 54.61 H 5.90 N 6.07 Cl⁻ 15.35 $Cl_{tot}$ 23.03
Found : 54.67 5.91 6.03 15.34 23.28

14. Dextrorotatory dihydrochloride of 2-[2-[4-[(4-chlorophenyl) phenylmethyl]-1-piperazinyl]ethoxy]acetic acid.

The dextrorotatory dihydrochloride of 2-[2-[4-[(4-chlorophenyl)phenylmethyl] -1-piperazinyl]ethoxy]acetic acid is prepared according to the method described at point 13 above, starting with 25.2 g (0.065 mole) of levorotatory (−)-2-[2-[4-[(4-chlorophenyl)phenylmethyl]-1-piperazinyl] ethoxy]acetamide (prepared at point 9 above). 25.6 g of the desired product are thus obtained.

M.P. : 227.9° Yield : 85.3%.
$[\alpha]_{365}^{25}$ : +12.87° (c=1, water).
Optical purity : 99.87%.
Analysis for $C_{21}H_{25}ClN_2O_3 \cdot 2HCl$ % :
Calc. : C 54.61 H 5.90 N 6.07 Cl⁻ 15.35 $Cl_{tot}$ 23.03
Found: 54.71 5.92 6.04 15.34 23.19

15. Dextrorotatory dihydrochloride of 2-[2-[4-[(4-chlorophenyl)phenylmethyl]-1-piperazinyl] ethoxy]acetic acid.

13.75 g (0.00216 mole) of the levorotatory dimaleate of methyl 2-[2-[4-[ (4-chlorophenyl)phenylmethyl]-1-piperazinyl]ethoxy]acetate (prepared at point 11 above) are added with stirring and at ambient temperature to 54 ml of a 2N aqueous solution of sodium hydroxide. The reaction mixture is extracted successively with100 ml and 75ml of diethylether and the organic phases are combined. This organic phase is dried over anhydrous sodium sulfate, filtered and the filtration residue is washed with 50 ml of diethylether. The organic phases are combined and the diethylether is evaporated. The oil thus obtained (8.4 g) is taken up in 50 ml of ethanol and 1.3 g (0.0229) of solid potassium hydroxide are added thereto. The mixture is heated for one hour at reflux temperature and then allowed to return to ambient temperature, then filtered and the filtrate is evaporated. The residue is taken up in 50 ml of water and concentrated in a rotating evaporator to remove residual ethanol. 10 ml of water are added to the partially concentrated solution and the pH of the solution is brought to a value of between 4 and 5 by addition of a 10% aqueous solution of hydrochloric acid. The resulting solution is extracted with 50 ml of dichloromethane, the pH of the solution is again brought to a value of between 4 and 5 by addition of a 10% aqueous solution of hydrochloric acid and the solution is once again extracted with 50 ml of dichloromethane. The organic phases are combined and dried over anhydrous magnesium sulfate, filtered and the dichloromethane is evaporated. The viscous oil thus obtained (9.8 g) is dissolved in 68.6 ml of acetone and the slightly cloudy solution is treated with 1 g of activated charcoal and filtered while hot through diatomaceous earth. 3.6 ml (0.043 mole) of concentrated hydrochloric acid are added to the hot clear yellow solution thus obtained. The suspension is allowed to cool to ambient temperature with stirring and stirring of the suspension is continued for one hour at 0° C. The precipitate which forms is filtered off, washed with 50 ml of acetone and dried under vacuum at 40° C. 6.8 g of the dextrorotatory dihydrochloride of 2-[2-[4-[(4-chlorophenyl) phenylmethyl]-1-piperazinyl] ethoxy]acetic acid are thus obtained.

M.P. : 227.8° C. Yield: 70.8%.
$[\alpha]_{365}^{25}$ : +13.7° (c=1, water).
Optical purity : ≈100%.
Analysis for $C_{21}H_{25}ClN_2O_3 \cdot 2HCl$ in % :
Calc. : C 54.61 H 5.90 N 6.07
Found : 54.18 6.02 5.68

The following compounds have been subjected to pharmacological tests, the results of which are given hereinafter.

(−)-1-[(4-chlorophenyl)phenylmethyl]piperazine (compound A, prepared in Example 4.1);

(+)-1-[(4-chlorophenyl)phenylmethyl]piperazine (compound B, prepared in Example 4.2);

levorotatory dihydrochloride of 1-[(4-chlorophenyl)phenylmethyl]4-[(3-methylphenyl)methyl] piperazine (compound C, prepared in Example 5.1);

dextrorotatory dihydrochloride of 1-[(4-chlorophenyl)phenylmethyl]-4-[ (3-methylphenyl)methyl]piperazine (compound D, prepared in Example 5.2);

levorotatory dihydrochloride of 1-[(4-tert-butylphenyl)methyl]-4-[(4chlorophenyl)phenylmethyl] piperazine (compound E, prepared in Example 5.3);

dextrorotatory dihydrochloride of 1-[(4-tert-butylphenyl)methyl]-4-[(4chlorophenyl)phenylmethyl] piperazine (compound F, prepared in Example 5.4);

levorotatory dihydrochloride of 2-[2-[4-[(4-chlorophenyl)phenylmethyl]- 1-piperazinyl]ethoxy]ethanol (compound G, prepared in Example 5.5);

dextrorotatory dihydrochloride of 2-[2-[4-[(4-chlorophenyl)phenylmethyl] -1-piperazinyl]ethoxy]ethanol (compound H, prepared in Example 5.6);

levorotatory dihydrochloride of 2-[2-[2-[4-[(4-chlorophenyl)phenylmethyl] -1-piperazinyl]ethoxy]ethoxy]ethanol (compound I, prepared in Example 5.7);

dextrorotatory dihydrochloride of 2-[2-[2-[4-[(4-chlorophenyl)phenylmethyl] -1-piperazinyl]ethoxy]ethoxy] ethanol (compound J, prepared in Example 5.8);

(−)-2-[2-[4-[(4-chlorophenyl)phenylmethyl]-1-piperazinyl] ethoxy]acetamide (compound K, prepared in Example 5.9);

(+)-2-[2-[4-[(4-chlorophenyl)phenylmethyl]-1-piperazinyl] ethoxy]acetamide (compound L, prepared in Example 5.10);

levorotatory dimaleate of methyl 2-[2-[4-[(4-chlorophenyl)phenylmethyl] -1-piperazinyl]ethoxy]acetate (compound M, prepared in Example 5.11);

dextrorotatory dimaleate of methyl 2-[2-[4-[(4-chlorophenyl)phenylmethyl] -1-piperazinyl]ethoxy]acetate (compound N, prepared in Example 5.12);

levorotatory dihydrochloride of 2-[2-[4-[(4-chlorophenyl)phenylmethyl]- 1-piperazinyl]ethoxy]acetic acid (compound O, prepared in Example 5.13) and dextrorotatory dihydrochloride of 2-[2-[4-[(4-chlorophenyl)phenylmethyl] -1-piperazinyl]ethoxy]acetic acid (compound P, prepared in Example 5.14).

1. Affinity towards the histamine $H_1$ receptor.

The affinity of these compounds towards the rat cortex histamine $H_1$ receptor has been determined using the method described by M. M. BILLAH et al., J. Pharmacol. Exp. Ther., 252 (3), (1990), 1090–1096.

These conventional assays involve the competitive binding to the histamine $H_1$ receptor of, on the one hand, the compound to be tested and, on the other hand, a radioligand, which in the particular case of the histamine $H_1$ receptor is [$^3$H]mepyramine, known to be a selective antagonist of this receptor.

Displacement curves of the binding of [$^3$H]mepyramine are plotted for various concentrations of the compounds to be tested ranging from $10^{-10}$ to $10^{-4}$ mole/l, and for a concentration of $4.5 \times 10^{-9}$ mole/l of [$^3$H]mepyramine (24.8 Ci/mmole, provided by New England Nuclear, Belgium).

Cerebral cortexes from male Sprague-Dawley rats are homogenized in 2 ml per cortex of a 20 mM Tris-HCl buffer (pH 7.4) containing 250 mM sucrose. The homogenates are centrifuged at 30,000 g for 30 minutes at 4° C. and the centrifugation pellets are resuspended in the same fresh buffer and preserved in liquid nitrogen.

In order to determine the binding to the $H_1$ receptor, the samples containing 0.5 mg of cortex membrane protein, in 0.5 ml of 50 mM Tris-HCl buffer (pH 7.4) containing 2 mM magnesium chloride, are incubated with [$^3$H]mepyramine and the compound to be tested, at 25° C. for 60 minutes. The bound [$^3$H]mepyramine is separated from the free radioligand by rapid filtration of the sample through a Whatman GF/C filter, previously impregnated for at least 2 hours with a 0.1% solution of polyethyleneimine, in order to reduce the possibility of non-specific binding of the radioligand with other proteins. The residue from the filtration is then washed four times with 2 ml of 50 mM Tris,HCl buffer (pH 7.4) and cooled in an ice bath. The radioactivity thereof is then measured using a β particle Tri-carb 1090 scintillation counter (Camberra-Packard, Belgium). Non-specific binding has been estimated in the presence of a 10 μM aqueous solution of cetirizine and represents 30% of the total binding. The $IC_{50}$ values of the compounds to be tested (concentrations in mole/l necessary to inhibit binding of the radioligand to the $H_1$ receptor by 50%) are determined by analysis of the competitive binding curves (A. DE LEAN et al., Mol. Pharmacol., 21 (1982), 5–16) and their inhibition constants ($K_i$) are calculated by means of the CHENG and PRUSOFF equation (Y. C. CHENG and W. H. PRUSOFF, Biochem. Pharmacol., 22 (1973), 3099–3108).

Table III below gives the values of $pK_i$ (cologarithm of $K_i$) calculated from $K_i$ (mean value±deviation with respect to the mean (n=2)), for the compounds tested.

TABLE III

| Compound | pKi |
| --- | --- |
| C | 6.2 ± 0.1 |
| D | 7.2 ± 0.2 |
| E | 5.9 ± 0.2 |
| F | 6.2 ± 0.0 |
| G | 7.6 ± 0.1 |
| H | 8.7 ± 0.0 |
| I | 7.1 ± 0.0 |
| J | 8.6 ± 0.0 |
| K | 8.6 ± 0.1 |
| L | 6.8 ± 0.1 |
| M | 7.1 ± 0.1 |
| N | 8.5 ± 0.1 |
| O | 7.4 ± 0.0 |
| P | 8.2 ± 0.0 |

From this Table, it can be seen that the compounds of formula V have good antihistaminic activity. These results also show that there is a difference, between the $pK_i$ values for the two enantiomers of one compound, which corresponds to a difference in relative affinity (thus in $K_i$) of a factor of between about 2 and 64 towards the rat cortex $H_1$ receptor. Such a difference indicates that the enantiomer, which has the greatest affinity for this type of receptor (for example compound J compared with the other enantiomer I), is to be used specifically as an anxiolytic or tranquilizing agent for the treatment of diseases which are caused by an excitation of the central nervous system.

2. Peripheral antihistaminic properties.

The peripheral antihistaminic properties of the compounds are determined by measuring the inhibition of the contraction of the isolated guinea pig trachea, caused by histamine, using the method described by M. H. AMIRI and G. GABELLA (Anat. Embryol., 178 (1988), 389–397).

Tracheas of Dunkin-Hartley guinea pigs of both sexes (weight: 250–500 g) are excised and cut into four fragments of three segments of cartilage each. These fragments are immersed in a Krebs-Heinseleit solution at 37° C. containing $10^{-7}$ mole/l of atropine and $10^{-5}$ mole/l of indomethacin and are stretched with a weight of 1 g. The solution is aerated with a current of oxygen containing 5% carbon dioxide. Each change in tension is recorded with an isometric force indicator K 30 (from Hugo Sachs Elektronik) coupled to an amplifier and a Sanborn 7700 recorder (from Hewlett Packard). The preparation (i.e. trachea fragment) so obtained is allowed to stabilize for one hour during which the base line for the tension is readjusted if necessary.

Each preparation is precontracted by the addition of $10^{-4}$ mole/l of histamine to the medium; the observed contraction is taken as a reference (100%). After washing and stabilization, a cumulative curve showing the effects of histamine, as a function of its concentration ($10^{-6}$, $10^{-5}$ and $10^{-4}$ mole/l) is plotted as a control.

For the same preparation, four further cumulative curves showing the effects of histamine as a function of its concentration are then recorded at four increasing concentrations of each compound to be tested.

The compounds to be tested are incorporated in the medium five minutes before the histamine. Between each measurement, the preparations are washed at least four times with an interval of five minutes between each washing. Each compound is tested on at least 6 trachea fragments. When the last curve is plotted, additional concentrations of $3.2\times10^{-4}$ and $10^{-3}$ mole/l of histamine are added in order to determine whether the antagonism is competitive or not.

When non-competitive inhibition is observed, $pD_2$, is calculated, i.e. the cologarithm of the concentration of the compound tested which causes a 50% inhibition of the maximum recorded contraction (J. M. VAN ROSSUM, Arch. Int. Pharmacodyn., 143 (1963), 299–330). When competitive inhibition is observed, $pA_2$ is calculated, i.e. the cologarithm of the concentration of the compound tested which requires the histamine dose to be doubled in order to obtain the same contraction effect.

Table IV below gives the $pA_2$ or $pD_2$, calculated for the compounds tested (mean value±standard deviation).

TABLE IV

| Compound | $pA_2$ | $pD_2$, |
|---|---|---|
| A | 5.7 ± 0.4 | — |
| B | 5.0 ± 0.1 | — |
| G | 6.5 ± 0.3 | — |
| H | — | 6.7 ± 0.1 |
| I | 6.5 ± 0.4 | — |
| J | — | 6.0 ± 0.3 |
| K | — | 6.3 ± 0.2 |
| L | 6.4 ± 0.2 | — |
| O | 6.6 ± 0.3 | — |
| P | — | 6.3 ± 0.2 |

This test reveals a surprising characteristic for the tested levorotatory and dextrorotatory enantiomer pairs. With the exception of the pair of enantiomers A and B, it is found for all the other pairs, that one enantiomer is a competitive inhibitor, whilst the other is a non-competitive inhibitor. This clearly demonstrates the advantage of preparing optically pure derivatives of 1-[(4-chlorophenyl)phenylmethyl] piperazine.

The advantage of the competitive inhibitors stems from the fact that they have generally a lower affinity towards the rat cortex $H_1$ histamine receptor, which predicts that the anti-allergic properties of these compounds are associated, very little or not at all, to undesirable effects on the central nervous system, such as for example sedation or drowsiness. Noncompetitive inhibitors have the advantage of being able to inhibit the effects of histamine, even when the latter is present in high local concentrations. They, thus, are better indicated for the topical treatment of diseases of the skin or the mucous membranes.

3. Inhibition of the cutaneous reaction induced by histamine in dogs.

The dog is considered, among the animal species, to be the species having a sensitivity to histamine relatively close to that of man. Thus, it is considered that the antihistaminic activity of a compound, observed;in the dog, is predictive of the activity which would be observed in man.

In this test, nine Beagle dogs are used, having an average weight of 12.6 kg and of about two years of age and of which the abdomens have been locally shaved. 50 μl of a 0.9% aqueous solution of sodium chloride, containing 10 μg/ml of histamine, is injected intradermally into the shaved area. Simultaneously, a solution of Evans blue dye (60 mg/ml in a 0.9% aqueous solution of sodium chloride), is administered by intravenous injection to each dog at a dose of 0.1 ml/kg. An allergic reaction develops at the intradermal injection site and there appears a wheal, the area of which is measured exactly 30 minutes after the two injections. This area is taken as the reference area (100%).

The compound to be tested is then administered orally, at a dose of 0.15 mg/kg ($0.32\times10^{-6}$ mole/kg). 0.5, 1.5, 3, 6, 9, 12, 24 and 32 hours after administration of the compound to be tested, new wheals are induced at different abdominal locations by injecting histamine. Each time, the area of the induced wheal is measured 30 minutes after the injection of histamine.

The antihistaminic activity of a compound on the cutaneous allergic reaction is determined by measuring the reduction in the area of the induced wheals, following administration of the compound, with respect to the area of the reference wheal, and then expressed in percent.

Table V below, gives the antihistaminic activity obtained for compound P.

In this table, the first column indicates the time, expressed in hours elapsed since administration of the tested compound;

the second column, the area, expressed in mm² of the wheals induced by histamine (mean observed for nine dogs±standard deviation);

the third column, the reduction (in percent) in the area of the wheals observed with time, with respect to the reference area and;

the fourth column, the statistical significance of the effect observed with time, evaluated by means of the Wilcoxon test.

TABLE V

| Time (hours) | Area of wheals (mm²) | Reduction in area (%) | Statistical value |
|---|---|---|---|
| 0 | 76 ± 8 | 100 | |
| 0.5 | 65 ± 10 | 85 | $p \leq 0.01$ |
| 1.5 | 44 ± 12 | 58 | $p \leq 0.001$ |
| 3 | 33 ± 10 | 43 | $p \leq 0.001$ |
| 6 | 41 ± 13 | 54 | $p \leq 0.001$ |
| 9 | 41 ± 10 | 54 | $p \leq 0.001$ |
| 12 | 41 ± 10 | 54 | $p \leq 0.001$ |
| 24 | 45 ± 5 | 59 | $p \leq 0.001$ |
| 32 | 51 ± 5 | 67 | $p \leq 0.01$ |

It can be seen that the reduction in the area of the wheals, observed 30 minutes after administration of compound P, is 15%. Maximum inhibition is observed after three hours and reaches 57%. After 32 hours, a statistically significant inhibition of 33% is still observed.

4. Toxicity.

The compounds of formula V have low toxicity. The lethal dose (causing death in 2 out of 3 mice following intraperitoneal injection of the compounds) is appreciably higher than the dose required to inhibit the cutaneous reaction induced by histamine in the dog. Table VI gives the values for the lethal doses (in mice) for the compounds of formula V.

TABLE VI

| Compound | Lethal dose (mole/kg) |
|---|---|
| C | $>1 \times 10^{-3}$ |
| D | $>1 \times 10^{-3}$ |
| E | $1 \times 10^{-3}$ |
| F | $>1 \times 10^{-3}$ |
| G | $6 \times 10^{-4}$ |
| H | $6 \times 10^{-4}$ |
| I | $1 \times 10^{-4}$ |
| J | $1 \times 10^{-4}$ |
| K | $3 \times 10^{-4}$ |
| L | $1 \times 10^{-3}$ |
| O | $3 \times 10^{-4}$ |

TABLE VI-continued

| Compound | Lethal dose (mole/kg) |
|---|---|
| P | $3 \times 10^{-4}$ |

5. Posology and administration.

The compounds of formula V have, in particular, antiallergic and antihistaminic activity as well as tranquilizing and anxiolytic activity. Pharmaceutical compositions containing these compounds may be administered orally, parenterally or rectally. They may also be administered in a nasal spray or instillations (aerosols) or in the form of a cream or ointment.

For oral administration, solid or liquid forms are used such as tablets, gelatine capsules, sugar-coated pills, granulated materials, solutions, syrups, etc.

For parenteral administration, aqueous or oily solutions, suspensions or emulsions can be suitable.

For rectal administration, suppositories are used.

The pharmaceutical forms listed above are prepared using methods currently used by pharmacists and can contain traditional excipients in pharmaceutically non-toxic amounts, such as dispersants, stabilizers, preservative agents, sweeteners, coloring agents and the like.

The percentage of active compound can vary within wide limits, depending upon the mode of administration and in particular the frequency of administration. As regards the daily dosage, this can vary within a wide range of from 0.5 to 100 mg, preferably between 2 and 20 mg of active compound per day.

We claim:

1. A compound selected from the group consisting of the levorotatory enantiomer of 1-[(4-chlorophenyl)phenylmethyl]-4-[ (4-methylphenyl)sulfonyl]piperazine of the formula

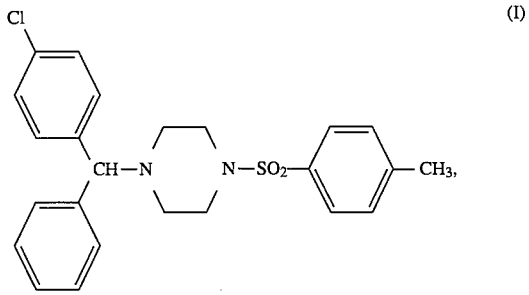

and the dextrorotatory enantiomer of 1-[(4-chlorophenyl)phenylmethyl ]-4-[(4-methylphenyl)sulfonyl]piperazine of the formula I.

2. A compound according to claim 1, said compound being levorotatory (−)-1-[(4-chlorophenyl)phenylmethyl]-4-[(4-methylphenyl )sulfonyl]piperazine.

3. A compound according to claim 1, said compound being dextrorotatory (+)-1-[(4-chlorophenyl)phenylmethyl] -4-[(4-methylphenyl )sulfonyl]piperazine.

* * * * *

UNITED STATES PATENT AND TRADEMARK OFFICE
CERTIFICATE OF CORRECTION

PATENT NO. : 5,478,941
DATED : December 26, 1995
INVENTOR(S) : ERIC COSSEMENT, GUY BODSON and JEAN GOBERT It is certified that error appears in the above-indentified patent and that said Letters Patent is hereby corrected as shown below:

Column 18, in TABLE III, the righthand column under the heading "pKi", for compound M change "7.1 ± 0.1" to read —8.5 ± 7.1—;

for compound N, change "8.5 ± 0.1" to read —7.1 ± 0.1—.

Signed and Sealed this

Fourteenth Day of January, 1997

Attest:

BRUCE LEHMAN

*Attesting Officer*     *Commissioner of Patents and Trademarks*